(12) United States Patent
Makdissi et al.

(10) Patent No.: US 11,793,485 B2
(45) Date of Patent: Oct. 24, 2023

(54) CATHETER WITH BUILT-IN ULTRASOUND IMAGING SENSORS

(71) Applicant: CAIRDAC, Antony (FR)

(72) Inventors: Alaa Makdissi, Paris (FR); Willy Regnier, Longjumeau (FR); Guillaume Ferin, Tours (FR); An Nguyen-Dinh, La Riche (FR)

(73) Assignee: CAIRDAC, Antony (FR)

( * ) Notice: Subject to any disclaimer, the term of this patent is extended or adjusted under 35 U.S.C. 154(b) by 293 days.

(21) Appl. No.: 17/100,799

(22) Filed: Nov. 20, 2020

(65) Prior Publication Data

US 2021/0153842 A1    May 27, 2021

(51) Int. Cl.
| | | |
|---|---|---|
| *A61B 8/12* | (2006.01) | |
| *A61B 8/00* | (2006.01) | |
| *A61M 25/00* | (2006.01) | |
| *A61N 1/375* | (2006.01) | |
| *A61B 1/00* | (2006.01) | |

(52) U.S. Cl.
CPC ................ *A61B 8/12* (2013.01); *A61B 8/445* (2013.01); *A61B 8/4494* (2013.01); *A61M 25/0045* (2013.01); *A61N 1/3756* (2013.01); *A61B 1/0008* (2013.01)

(58) Field of Classification Search
CPC ......... A61B 8/445; A61B 8/12; A61B 8/4494; A61B 5/6853; A61B 1/0008; A61B 8/0883; A61B 8/0891; A61M 25/0045; A61M 2025/09008; A61M 25/10; A61N 1/3756; A61J 15/0049; B29L 2031/7543; A61F 2/2433

See application file for complete search history.

(56) References Cited

U.S. PATENT DOCUMENTS

| | | | | |
|---|---|---|---|---|
| 3,626,950 | A * | 12/1971 | Schulte | A61M 25/04 |
| | | | | 604/268 |
| 4,754,752 | A * | 7/1988 | Ginsburg | A61B 18/08 |
| | | | | 604/113 |
| 6,241,744 | B1 * | 6/2001 | Imran | A61B 8/0833 |
| | | | | 606/167 |
| 2007/0197918 | A1 * | 8/2007 | Vitek | A61N 7/022 |
| | | | | 600/459 |

(Continued)

FOREIGN PATENT DOCUMENTS

WO    WO2006091597    8/2006

*Primary Examiner* — Sean D Mattson
*Assistant Examiner* — Michael Yiming Fang
(74) *Attorney, Agent, or Firm* — CRGO Global; Steven M. Greenberg (57) ABSTRACT

The instrument includes a dual-wall deformable tube, with an inner sleeve, a coaxial outer sleeve, and an imaging module connected to the inner and outer sleeves. An array of transducers is carried by an outer face of the imaging module. The inner sleeve and the outer sleeve are mobile in relative axial translation between: a folded position in which the inner and outer sleeves both have a cylindrical shape, and in which the imaging module substantially extends in the continuation of the inner sleeve; and an expanded position, in which the inner sleeve has a cylindrical shape and the outer sleeve has a flared shape widening on the distal side and in which the imaging module substantially extends with the face that carries the transducers of the array turned in axial direction towards the front of the deformable tube.

14 Claims, 4 Drawing Sheets

(56) References Cited

U.S. PATENT DOCUMENTS

| | | | | |
|---|---|---|---|---|
| 2014/0180126 A1* | 6/2014 | Millett | ............... | G01N 29/2418 |
| | | | | 600/478 |
| 2015/0196309 A1 | 7/2015 | Matsubara et al. | | |
| 2017/0340877 A1* | 11/2017 | Ollivier | ................ | A61N 1/3756 |
| 2019/0321175 A1* | 10/2019 | Zhou | ................. | A61M 25/0662 |
| 2019/0344054 A1* | 11/2019 | Slattery | .......... | A61B 17/320725 |
| 2020/0383661 A1* | 12/2020 | Gijsbers | ............... | A61B 8/4477 |
| 2022/0183698 A1* | 6/2022 | Backeris | .......... | A61B 17/12186 |

* cited by examiner

CATHETER WITH BUILT-IN ULTRASOUND IMAGING SENSORS

CROSS REFERENCE TO RELATED APPLICATIONS

This application claims priority under 35 U.S.C. § 119(a) to French patent application number 19315138.8, filed on Nov. 22, 2019, the entire teachings of which are incorporated herein by reference.

BACKGROUND OF THE INVENTION

Field of the Invention

The invention relates to an instrument for intracorporeal exploration and intervention, placed at the end of a catheter introduced into the body of a patient and carrying at its distal end an array of transducers capable of being steered towards an exploration or intervention site, and more specifically more specifically to a hollow catheter with, over its whole length, an inner axial lumen that opens to the distal side facing the exploration or intervention site.

Description of the Related Art an autonomous implantable capsule.

An "autonomous capsule", "leadless capsule" or simply "capsule", is in the form of a capsule implanted into a heart chamber (ventricle, atrium or even left arterial heart chamber). The capsule is autonomous, i.e. it is devoid of any physical connection to a main device, whether the latter is an implanted device (such as a stimulation pulse generator casing) or a non-implanted device (external peripheral device such as a programming or monitoring device for remote follow-up of the patient). For that reason, this type of device is the "leadless", to distinguish it from electrodes or sensors arranged at the distal end of a conventional lead, along the whole length of which run one or several conductors galvanically connecting the electrode or the sensor to a generator connected to an opposite, proximal end of the lead. US 2009/0171408 A1 (Solem), US 2017/0151429 A1 (Regnier) and WO 2018/122244 A1 (Regnier) describe various examples of such intracardiac leadless capsules.

The implantation of such endocavitary capsules involves major constraints, in particular due to the method of approach that requires passing through the peripheral venous network. Indeed, due to the relatively large dimensions of present leadless capsules, which have a typical diameter of about 4 to 7 mm for a length of 15 to 40 mm, with a device of such a size there exists no upper-way procedure, i.e. via the subclavian vein, to accede to a heart chamber, in particular to reach the bottom of the right ventricle. It is hence necessary to use a different access, starting from a femoral puncture site, then going along the inferior vena cava up to the heart.

The problem is the same if it is desired to proceed to the explantation of a capsule already in place, whether it is to fully remove it or to reposition it at a nearby site (hereinafter, reference will simply be made to "implantation" of a capsule, it being understood that this also refers to the reverse, explantation operation).

For that purposes there exist "steerable" catheters, which are well-known implantation tools whose distal end is operable from a handle located at the opposite end, on the proximal side, to allow such a steering operation at the atrium, under image intensifier.

Such a steerable catheter and the way to operate the implantation are described in particular in US 2014/0378991 (Ollivier). The implantation tool disclosed in this document includes a cylindrical protective housing distally extending the steerable catheter and containing the capsule to be implanted. This capsule is coupled to a secondary catheter (or "delivery catheter") inserted in the inner central lumen of the main catheter (or "guide catheter"), and is maintained in retracted position within the tip o the latter during the whole duration of the approach operation. The capsule and the delivery catheter are temporary connected by a simple releasable mechanism allowing a complete screwing of the capsule into the heart wall then the final release thereof. The telescopic configuration of the delivery catheter allows pushing the capsule out of the protective tip and beyond the latter over several centimeters, permitting in any case a complete and accurate approach of the capsule up to the bottom of the ventricle.

The problem to be solved lies in the fact that, in many intervention or implantation techniques, the presence of an inner lumen of relatively large diameter (for the introduction of the medical device, possibly provided with a protective sleeve, or for the instrument to be moved up to the intervention site) does not make it possible to place the transducers of the array at the distal end of the catheter, at which this lumen opens, in the same way as with conventional imaging probes. Indeed, in these conventional probes, for example those of ultrasound imaging endoscopic devices used in laparoscopy, the transducers of the array are arranged on a disc-shaped flat support extending in a radial plane. Actually, the intervention then requires the introduction of two catheters, i.e. a catheter for collecting an ultrasound image, and one (or several) other catheter(s) carrying the surgical instruments.

In the case of an approach through the venous network, it is not conceivable to introduce several catheters side-by-side. If it is desired to gather into a single and same tool the two functions—exploration by the array of transducers and intervention through the inner axial lumen—it is then necessary to use a bidimensional array of transducers mounted around the central lumen, on a support face turned towards the implantation or intervention site.

US 2008/0221448 A1 (Khuri-Yakub et al.) describes such a structure including a hollow catheter head, carrying at the front periphery thereof a crown of ultrasound transducers adapted to collect, after suitable image processing, a representation of the target body site in order to guide and assist the surgical intervention, in this case local ablation of tissues. The drawback of this device is its very large overall diameter, due in particular to the presence of the crown of transducers at the distal end, which diameter adds to that of the catheter itself. With such a configuration, if it is desired to use this device for an intervention with an approach through the venous network, either the excessive overall diameter would forbid this approach, or the inner lumen would have a too small diameter to introduce therein a leadless capsule to be implanted, the diameter of which could typically reach 4 to 7 mm, as indicated hereinabove, not to mention the additional diameter of the housing in which this capsule is housed. In any event, if the front surface occupied by the array of transducers is too reduced, the resolution of the image obtained will be excessively degraded.

Another approach is described in WO 2017/144288 A1 (Koninklijke Philips NV), in which the transducers of the array are not placed on a front face of the catheter, but on retractable elongated supports radiating from the centre of the catheter, at the distal end thereof, these supports expanding "like flower petals" once the vicinity of the intervention site is reached. It is hence possible to have, after the expansion, a relatively extended array of ultrasound transducers that allows obtaining a rather accurate image of the target site, for example a tumor towards which are focused the transducers of the different expanded "petals". The instrument for ablating the tumor is introduced through a central lumen of the catheter which, as a variant, may also serve for supplying a cooling fluid or balloon inflating fluid.

The making of such a system is however delicate and expensive, insofar as it is necessary to design an articulated mechanical system for expanding the "petals" with respect to the catheter body. Moreover, the tilt of the arrays of conductors carried by the expanded petals will have a non-negligible effect on the accuracy and quality of the ultrasound image eventually obtained by means of these transducers.

US 2014/0180126 A1 describes another type of exploration probe, in which an imaging sensor is integrated to the wall of an outer tube, in the form of an inflatable balloon, of a stent delivery intravascular catheter. This arrangement makes it possible to explore the region of implantation when the balloon is inflated, so as to be able to possibly readjust the positioning of the latter in the vessel.

BRIEF SUMMARY OF THE INVENTION

The invention sets forth for that purpose an instrument for intracorporeal exploration and intervention including a double-wall deformable tube including: an inner sleeve extending from a proximal end to a distal end, and defining an axial lumen opening on the distal side and on the proximal side; an outer sleeve, coaxial to an inner sleeve and extending from a proximal end to a distal end; and an imaging module, connected at the inner periphery to the distal end of the inner sleeve and at the outer periphery to the distal end of the outer sleeve. The instrument also includes an array of transducers, carried by an outer support face of the imaging module.

The inner sleeve and the outer sleeve are mobile in relative axial translation between a folded position, in which the inner sleeve and the outer sleeve both have a cylindrical shape and in which the imaging module substantially extends in the continuation of one of the inner sleeve or the outer sleeve; and an expanded position, in which one of the inner sleeve has a cylindrical shape and the other of the inner sleeve or the outer sleeve has a flared shape widening on the distal side and in which the imaging module substantially extends with the face that carries the transducers of the array turned in axial direction towards the front of the deformable tube.

According to various advantageous subsidiary features:
the transducers of the array are ultrasound transducers and are mounted on the imaging module with the axis of their radiation pattern directed perpendicular to the support face;
in folded position, the respective proximal ends of the inner sleeve and of the outer sleeve are moved closer to each other, and the imaging module substantially extends in the continuation of the inner sleeve, at least a part of the face of the imaging module that carries the transducers of the array being directed radially towards the inside of the deformable tube; and, in expanded position, the respective proximal ends of the inner sleeve and of the outer sleeve are spaced apart from each other, the face of the imaging module that carries the transducers of the array extending at least partly in a radial plane in which the transducers are directed in an axial direction parallel to the central axis of the deformable tube;
in particular and advantageously, in expanded position, the face of the imaging module that carries the transducers of the array extends with a part of the transducers directed in an axial direction parallel to the central axis of the deformable tube, and another part of the transducers directed in an inclined direction crossing the central axis of the deformable tube;
the imaging module includes a flexible printed circuit carrying and interconnecting the transducers of the array, wherein this flexible printed circuit can advantageously be extended on the proximal side by one or several ribbons extending up to a proximal end of the deformable tube and beyond, the ribbons carrying conductive tracks for the connection to the transducers of the array;
the deformable tube includes a set of parallel flexible lamellas each extending in an axial plane, each of these lamellas being formed of a single part made of an elastic material, in particular a metal or a metallic alloy, and extending from the proximal end of the inner sleeve up to the proximal end of the outer sleeve by being folded over itself at the imaging module;
the inner sleeve and the outer sleeve each include a ring at their respective proximal end, a displacement of the two rings in relative axial translation making a transition between the folded position and the expanded position;
the instrument further includes a steerable catheter extending the deformable tube at its proximal end and including a mobile tube housed within an intermediate tube.

The mobile tube and the intermediate tube are coaxial to each other, extend from a proximal end to a distal end of the catheter and are mounted telescopically into each other with possibility of mutual rotation and mutual axial translation, and the inner sleeve and the outer sleeve are connected in proximal part to, respectively, the mobile tube and the intermediate tube of the catheter.

In particular and advantageously, the inner sleeve can be detachably connected to the mobile tube of the catheter, in particular by means of a tip including a member for coupling the mobile tube of the catheter to an implantable autonomous capsule adapted to be housed within the axial lumen of the inner sleeve.

Advantageously, this tip is able to be uncoupled from the inner sleeve under the effect of a rotation of the mobile tube in the intermediate tube of the catheter, the tip remaining coupled to the inner sleeve during an axial translation of the mobile tube within the intermediate tube of the catheter.

In another embodiment, the mobile tube of the catheter may be connected to a surgical instrument adapted to be housed within the axial lumen of the inner sleeve.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION OF THE INVENTION

An exemplary embodiment of the invention will now be described with reference to the drawings.

Figure 1:
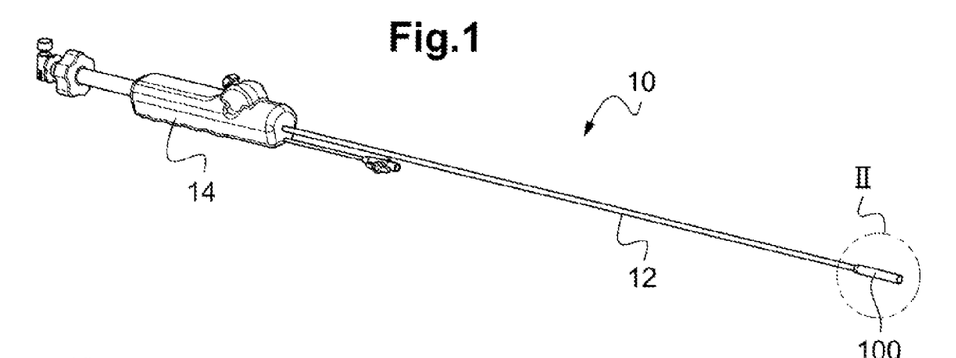
FIG. 1 is an overall view showing an instrument according to the invention, with a catheter tube associated, at its proximal end, with an operating handle usable by the practitioner in charge of the intervention.

FIG. 1 is an overall view of an instrument for intracorporeal exploration and intervention according to the invention. The instrument 10 includes a steerable catheter 12 connected at its proximal end to an operating handle 14 and at its opposite, distal end, to a surgical device intended to intervene on a site accurately located within the body of a patient, or to explore this site by an observation or imaging means for visualizing the region located in front of the distal end of the steerable catheter 12.

Here and hereinafter, the term "proximal" (or "rear") will be considered with respect to the instrument as a whole, i.e. towards the handle 14 operated by the practitioner; likewise, the term "distal" (or "front") will refer to an opposite direction, hence close to the intervention or exploration site. In the different appended figures, these proximal and distal directions correspond to the left and right, respectively. Likewise, the term "axial" will be used with reference to the axis Δ of the catheter 12, i.e. the greatest size of the latter, a "radial" direction being a direction located in a plane perpendicular to the axial direction Δ.

In a particular, non-limitative embodiment of the invention, which is that illustrated within the framework of the present disclosure and of the appended figures, the steerable catheter 12 is used to implant an autonomous leadless capsule 16 (FIGS. 4a to 4d and 5a to 5c) of the type described in introduction of the present disclosure.

It may in particular be a capsule to be implanted into the right ventricle of a heart, in the bottom of this ventricle, in the apex region. In this case, the access to the right ventricle is made through the vena cava, via the coronary sinus, then the tricuspid valve, according to a procedure well known in itself and described for example in United States Patent Application Publication No. 2014/0378991 by Ollivier. The steerable catheter 12 carries for that purpose, at its distal end, a tube or "housing" receiving and protecting the capsule during the progression in the venous network and during the passage through the valve, and protecting the surrounding tissues from the potential risks of tearing before the capsule reaches its definitive position facing the implantation site where the capsule will then be progressively expanded out of the housing 100 up to be docked to the heart wall.

The capsule 16 includes, in a manner known per se, a tubular body provided, at one of its ends, with a protruding helical anchoring screw 18 axially extending the tubular body and rotationally integral with the latter. The anchoring screw includes, in its distal portion, a length of about 1.5 to 2 mm of non-contiguous turns, intended to enter the heart tissue for securing the capsule thereto, and applying an electrode 20 against the tissues so as to be able to collect the cardiac depolarization signals and to potentially apply stimulation pulses at this place.

On the proximal side, the rear end 24 of the capsule is coupled to a catheter tip 22 forming a conjugated coupling member. The tip 22 is connected to an inner mobile tube 26 housed within an intermediate tube 28. The mobile tube 26 and the intermediate tube 28 are coaxial and extend from a proximal end to a distal end of the steerable catheter 12 by being telescopically mounted into each other with possibility of rotation and axial translation between each other. The intermediate tube 28 is integral with the body of the operating handle 14, whereas the inner tube 26 is moveable in rotation and translation with respect to the intermediate tube 28 by means of various levers and buttons at the disposal of the practitioner on the handle 14.

Such a catheter structure is in particular described in co-pending U.S. patent application Ser. No. 16/237,749, published as United States Patent Application Publication No. 2020/206465 A1, the content of which is hereby incorporated by reference, and as regards the handle, in co-pending U.S. patent application Ser. No. 16/416,201, the content of which is incorporated herein by reference.

Essentially, to implant the capsule, the practitioner makes the guide catheter 12 progress along the vena cava, then accurately steers the distal end of the latter until the docking of the distal end that carries the housing 100 to the bottom of the ventricle. Then, by means of the various levers and buttons of the handle, the practitioner operates a translation of the capsule in the distal direction, which expands the latter out of the housing 100. He then imparts to the capsule, via the inner tube 26 and the coupling tip 22, a combination movement of translation to press the distal end of the capsule against the wall, and of rotation to screw the capsule in order to anchor the latter into this wall. The rotation is continued until the front face of the capsule, that carries the electrode 20, comes and bears against the wall; this position is the definitive position of the capsule. The practitioner then uncouples the tip 22 carried by the inner tube 26 from the capsule, and proceeds to the removal of the guide catheter 12 out of the organism by a reverse operation with respect to that which had been implemented for the implantation.

The invention more particularly relates to the particular configuration of the distal end tube 100 which, in the illustrated application, is the housing surrounding and protecting the leadless capsule up to the implantation site.

This end tube must satisfy the dual constraint of:
being hollow, i.e. leaving free a large inner volume for housing the capsule to be implanted and allowing the sliding of the mobile inner tube 26 during the expansion of the capsule towards the implantation site; and
supporting, on a distal, front face, an array of transducers, for example ultrasound transducers, with the main axis of the radiation diagram of the transducers that can be directed towards the implantation site, so that an image of this site can be reconstructed from signals supplied by the transducers of the array and transmitted to an external imaging device for being processed by a suitable software and being displayed on a screen at the disposal of the practitioner.

The invention proposes to that end to make the tube 100 in the form of a deformable tube, like a glove finger. More precisely, the deformable tube 100 is a dual-wall tube, with:
an inner sleeve 102 (FIGS. 4a to 4d and 5a to 5c), extending from a proximal end to a distal end and defining an axial lumen, herein a housing volume receiving the leadless capsule 16, opening on the proximal side (towards the coupling tip 22 in the illustrated example) and on the distal side (towards the target implantation site);
an outer sleeve 104, coaxial with the inner sleeve and extending from a proximal end to a distal end; and
an imaging module 106, adjacent both to the inner sleeve 102 and to the outer sleeve 104, this imaging module 106 being of annular shape, connected at the inner periphery to the distal end of the inner sleeve and at the outer periphery to the distal end of the outer sleeve.

Figure 2:
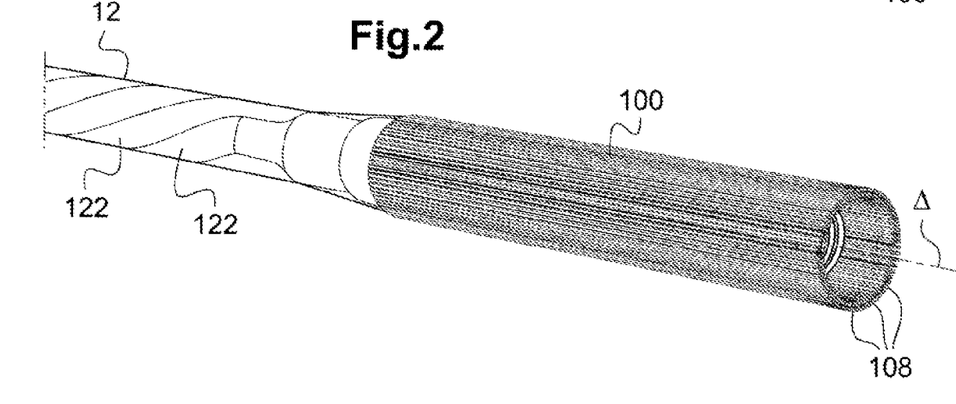
FIG. 2 is an enlarged view of the distal end of the catheter tube of the instrument according to the invention, corresponding to the detail referred II in FIG. 1.

Very advantageously, in a particular embodiment illustrated in particular in FIG. 2 and in FIGS. 4a to 4d, the deformable tube 100 is consisted of a set of parallel flexible lamellas each extending in an axial plane, along generating lines of the deformable tube 100. Each of the flexible lamellas 108 is formed of a single part made of an elastic material, for example a metal or a metallic alloy, advantageously titanium. Each of the lamellas 108 extends from the proximal end of the inner sleeve 102 to the proximal end of the outer sleeve 104 by being folded over itself at the imaging module 106. The proximal ends of the part of the lamellas 108 that forms the outer sleeve 104 are gathered together to an outer end ring 110, fastened at the distal end of the intermediate tube 28, whereas the proximal ends of the part of the lamellas 108 that forms the inner sleeve 102 are gathered together to an end ring 112 coupled, but not fastened, to the tip 22, and hence to the inner tube 26.

Figure 7A:
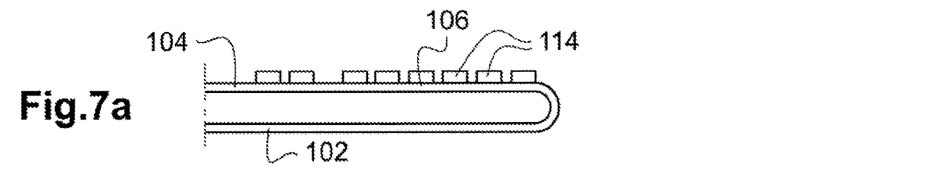
FIGS. 7a to 7c are isolated views of the distal end of the flexible circuit carrying the transducers and illustrating the progressive expansion of the flexible circuit and of the array of transducers, these figures corresponding to the detail referred VII in the respective FIGS. 4a to 5c.
Figure 7B:
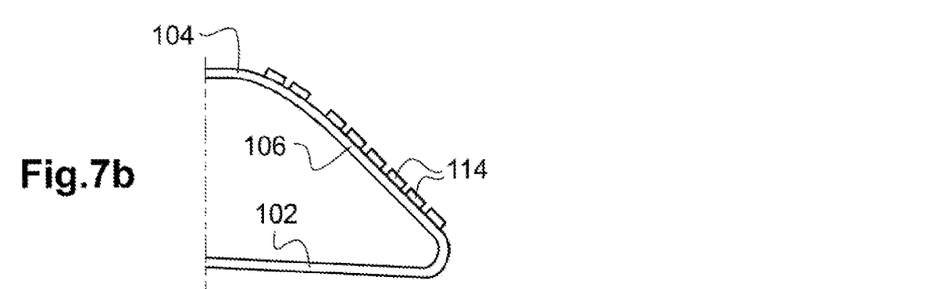
Figure 7C:
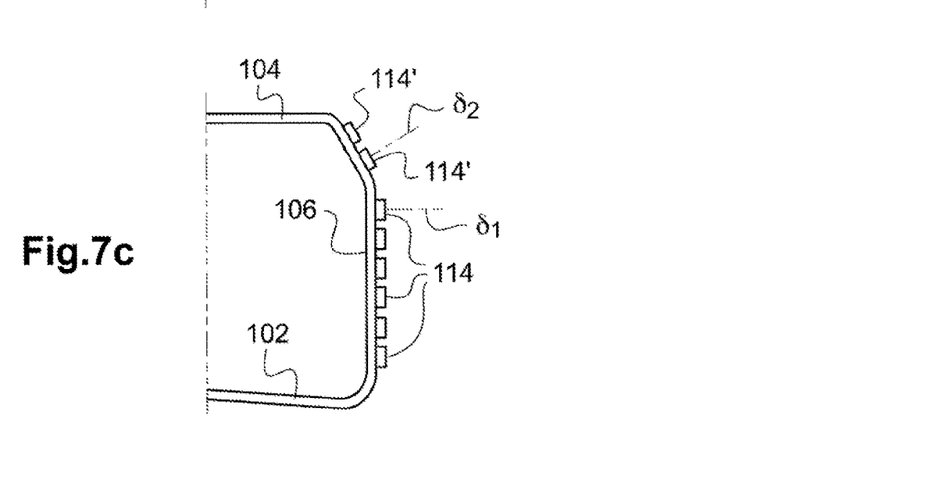

The imaging module 106 carries the array of transducers 114 (FIGS. 7a to 7c). These transducers are advantageously mounted on a flexible printed circuit 116 carrying and interconnecting the transducers of the array.

Figure 3:
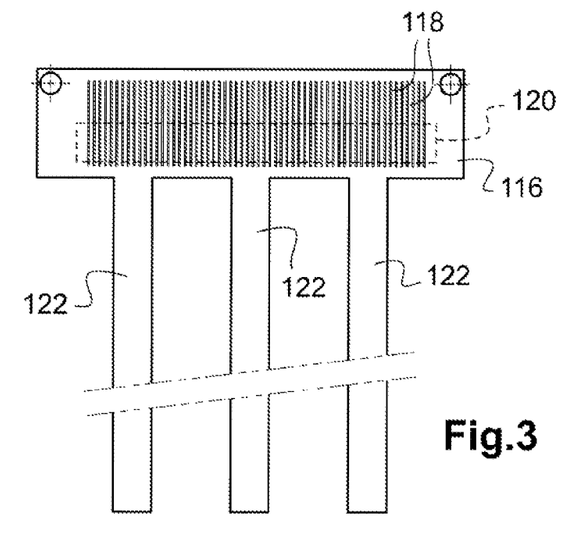
FIG. 3 is a schematic view of a flexible circuit carrying the array of transducers of the instrument of FIG. 2, as well as the conductors for the connection to these transducers, this flexible circuit being represented flat, in developed form.

An ultrasound transducer including chips added on a flexible circuit is described for example in United States Patent Application Publication No. 2004/0054289 A1, to which reference can be made for more details about the technological aspects of the embodiment. In the particular case of the invention, the flexible printed circuit 116 carries, as illustrated in FIG. 3, a series of conductive tracks 118 on which are added or cut out the transducer elements, for example CMUT (Capacitive Micromachined Ultrasonic Transducer) or piezoelectric chips. The transducers are mounted in an area 120 of the flexible circuit; the circuit carries for example eight lines of 64 columns forming a matrix array of 512 transducers, for example ultrasound transducers made in the form of elementary chips of 0.25× 0.25 mm.

The flexible printed circuit 116 is extended on the proximal side by one or several ribbons 122 carrying conductive tracks for the connection to the transducers of the array. The configuration of these ribbons makes it possible, as can be seen in FIG. 2, to wind them side-by-side at the surface of the steerable catheter 12, from one end to the other of the latter, which allows electrically connecting the transducers of the array located at the distal end to an electric connector located at the opposite, proximal end of the catheter 12 at the operating handle 14. The flexible printed circuit 116 can be a multilayer printed circuit to increase the number of connection conductors carried by each ribbon 122.

Advantageously, the thickness of the circuit is lower than 20 μm, so as not to hinder the deformation of the deformable tube 100, in particular at the imaging module 106, and to allow an easy winding of the ribbons 122 at the surface of the steerable catheter 12. Moreover, rigid portions may be hooked on all or part of the ribbons, both on the face on which are located the transducers and on the back of the device, to favour a reproducible and controlled folding. Bistable or shape-memory elements can also be installed under the active portion, to form a controllable curvature ensuring a geometric control of the focusing of the array of elements.

The kinematic of deformation of the dual-wall tube 100 will now be described, with reference in particular to FIGS. 4a to 4d (partially cutaway perspective views), 5a to 5c (corresponding to FIGS. 4a to 4c, in sectional view along an axial plane) and 7a to 7c (corresponding to the detail referred VII in FIGS. 5a to 5c, respectively).

Figure 4A:
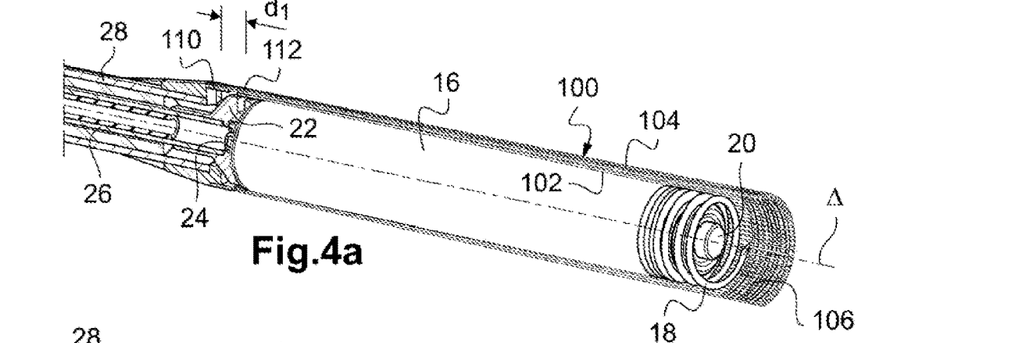
FIGS. 4a to 4d are perspective views, in partial cross-section, of the distal end of the catheter tube of FIG. 2, housing in its inner volume a leadless capsule to be implanted, these respective figures illustrating the successive positions taken by the unit during the operation of expansion of the array of transducers and the beginning of translation of the leadless capsule for implantation to the chosen site.
Figure 5A:
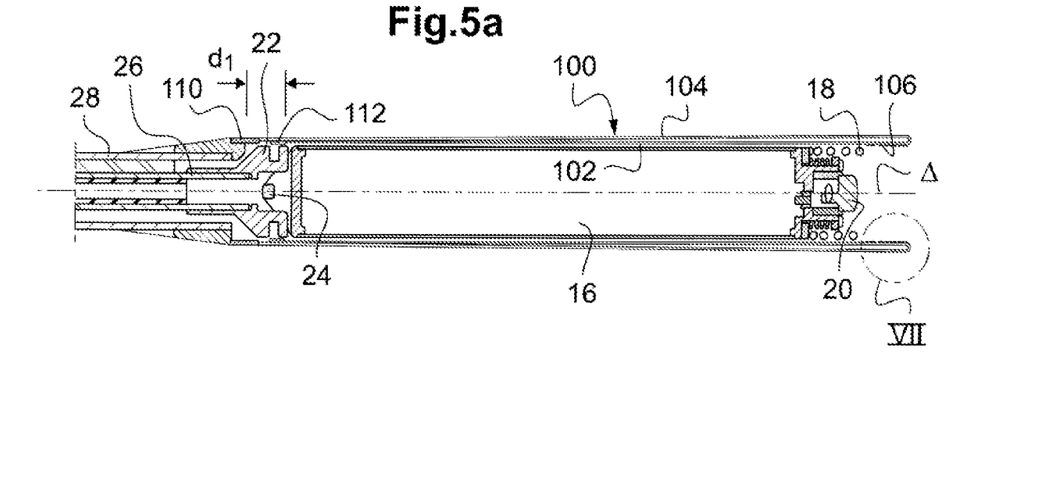
FIGS. 5a to 5c are cross-sectional views taken along an axial plane of the distal end of the catheter tube and of the leadless capsule, showing more accurately the development to the flexible circuit carrying the transducers and the front positioning of these latter once the array fully expanded.

The initial position, called folded position, is that illustrated in FIGS. 4a, 5a and 7a. In this position, the inner sleeve 102 and the outer sleeve 104 both have a cylindrical shape, and the imaging module 106 substantially extends in the continuation of the inner sleeve 102. More precisely, on the proximal side, the inner ring 112 is moved closer to the outer ring 110 by a distance $d_1$ and, on the distal side, the transducers 114 (cf. FIG. 7a), supported by the imaging module 106 are turned towards the inside of the tube 100, hence protected with respect to the outside. It will be noted, in this folded position, the existence of a significant safety margin in the distance between the end of the screw 18 of the leadless capsule and the end of the deformable tube 100 constituting the protective housing of this capsule; the surrounding body tissues are hence perfectly protected during the progression of the tube, for example in the venous network.

Figure 4B:
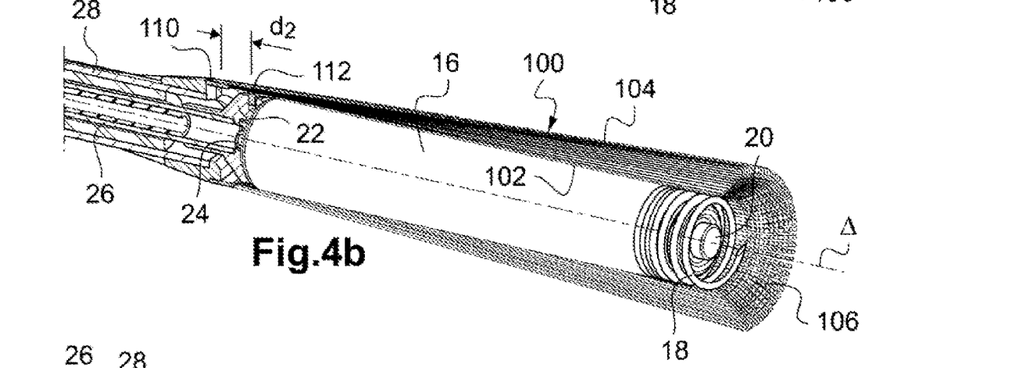
Figure 5B:
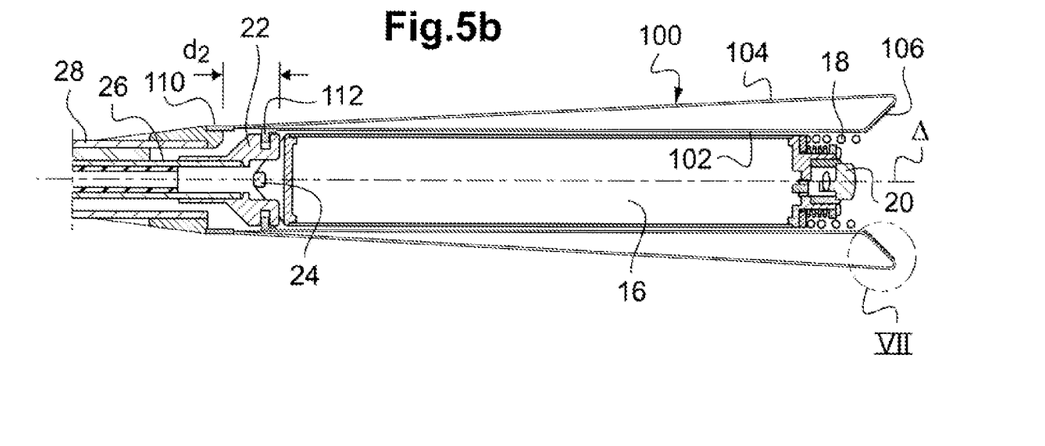

FIGS. 4b, 5b and 7b illustrate an intermediate position. In this position, the mobile inner tube 26 is progressively pushed forward inside the intermediate tube 28 by an operation of the practitioner from the handle 14 located out of the patient's body, at the end of the steerable catheter 18. This operation has for effect to move the inner ring 112 away from the outer ring 110, these two rings being then spaced apart by an axial distance $d_2$, higher than $d_1$.

Under the axial effort exerted by the mobile tube 26 when pushed by the practitioner, which folds the flexible lamellas

108 of the deformable tube 100, the structure will be progressively developed due to the constant developed length of the three contiguous elements consisted by (i) the inner sleeve 102, (ii) the imaging module 106 and (iii) the outer sleeve 104 (i.e. concretely, the total length of each of the flexible lamellas 108), as well as, by hinge effect at the junction (i) of the elements 102 and 106, and (ii) of the elements 102 and 104. The inner sleeve 102 keeps its cylindrical shape but, due to the above-mentioned constant developed length, the outer sleeve 104 is radially deformed towards the outside in its more distal part, taking a progressively conical shape, of axis Δ. It results therefrom a straightening of the module 106 that unfolds like a flower, by also taking a conical shape of axis Δ.

It will be noted that this flower shape can be made toroidal by addition of additional layers for managing the module constraint making it possible to modify in a controlled manner the deformation profile of the latter, as a function of a desired geometrical focus law for the array of transducers, going from the focusing to the defocusing to create a diverging beam.

Figure 4C:
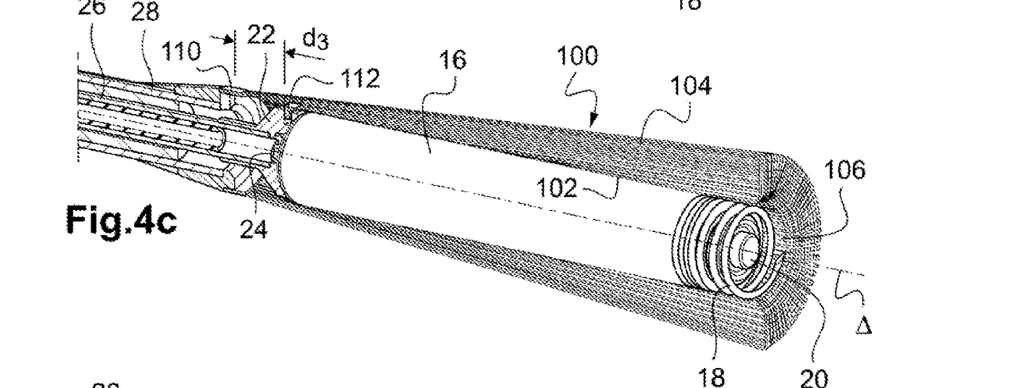
Figure 5C:
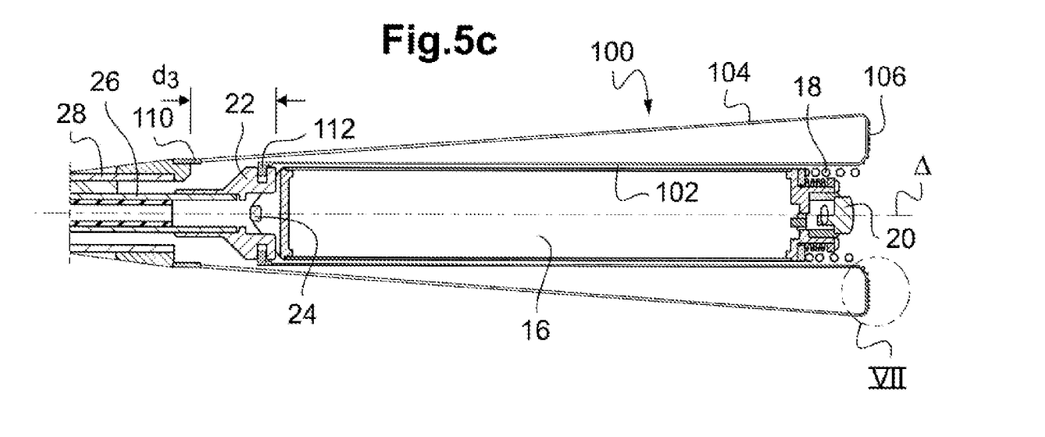

The final position, called expanded position, is that illustrated in FIGS. 4c, 5c and 7c. In this position, the inner sleeve 102 has always a cylindrical shape, the outer sleeve 104 has a conical shape, more flared than in the intermediate position of FIG. 5b, and the imaging module 106 now substantially extends with the face that carries the transducers 114 (cf. in particular FIG. 7c) turned forward in axial direction. The inner ring 112 and outer ring 110 are spaced apart by a distance $d_3$, higher than $d_2$. Typically, the full stroke $d_3-d_1$ of the inner ring 112 with respect to the outer ring 110 is about a few millimetres, for example $d_3-d_1=3.1$ mm.

In this expanded position, the transducers 114 have the main axis 61 of their radiation diagram directed parallel to the axis Δ, which functionally corresponds to a configuration of the transducer array of the front looking type. This configuration makes it possible to emit and receive signals that will provide, after a suitable imaging processing, a viewable representation of the implantation site opposite the end of the deformable tube 100, the latter always playing, in this position, the role of a housing that houses and protects the body of the leadless 16 to be implanted.

Advantageously, as more precisely illustrated in FIG. 7c, some of the transducers 114, referred 114', that are located close to the interface with the outer sleeve 104, have the main axis $\delta_2$ of their radiation diagram that is directed along an inclined direction with respect to the central axis Δ of the deformable tube 100, with for example an inclination of 30°. This makes it possible to collect imaging signals corresponding to points on the axis Δ in front of the end of the deformable tube 100, near the target implantation site.

It will be noted, in this expanded position, the small distance between the end of the screw 18 of the leadless capsule and the implantation site where this screw will have to be anchored.

Once the imaging signals collected and analysed, if the practitioner considers that the target implantation site is a satisfying site, he then proceeds to the extraction of the leadless capsule 16 out of its housing (consisted by the deformable tube 100 in the configuration of FIGS. 4c and 5c) and pushes the tip 22 in distal direction by continuing the axial translation movement of the inner tube 26 in the intermediate tube 28.

Once the end of the anchoring screw 18 in contact with the cardiac wall, the practitioner imparts to the mobile inner tube 26 a movement of rotation to anchor the capsule in place by screwing it into the tissues of this wall.

Advantageously, the system is arranged so that the continuation of this rotational movement automatically uncouples the tip 22 from the inner ring 112 to which it remained coupled during the above-described operation (coupling that would, precisely, allow the expansion in front of the implantation site of the imaging module 106 of the deformable tube 100, by translation of the mobile inner tube 26).

Figure 6:
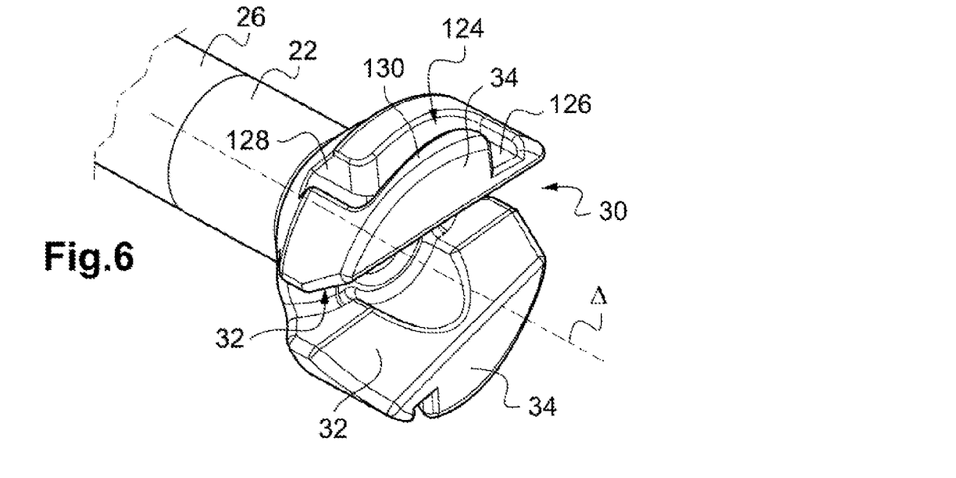
FIG. 6 is an enlarged perspective view of the tip carrying the member for the coupling to the leadless capsule and making it possible to operate the latter in translation and rotation and to simultaneously expand the array of transducers.

For that purpose, the tip 22 has a structure such as that illustrated in FIG. 6, that is derived from a tip shape described in co-pending U.S. patent application Ser. No. 16/655,198, the contents of which are incorporated herein by reference, with an imprint receiving the rear end 24 of the capsule 16 and consisted of an approximately V-shaped symmetrical recess 30, with two inclined faces 32 extending along planes located on either side of the central axis Δ into a symmetrical dihedron configuration, the axis of this dihedron extending in a radial direction. The tip 22 further includes a front surface turned toward the capsule, that is consisted of two front half-faces 34 that extend each respective inclined face 32 of the recess 30 in radial direction. The front half-faces 34 are inclined in opposite directions with respect to a radial plane, by an angle included between 5 and 15°, in one direction for one of the front half-face 34 and in the opposite direction for the other front half-face 34.

According to the present invention, the tip 22 further includes two peripheral cams 124 diagonally opposed, intended to receive two homologous diametrically opposed teeth of the inner ring 112. Each of these cams 124 has a S-shape, with (i) a first portion 126 opening forward and (ii) a second portion 128 opening rearward, these two portions being angularly offset, directed parallel to the axis Δ, and connected by (iii) a third portion 130 extending in a circumferential direction. The rotational movement imparted to the tip 22 during the screwing will hence have for effect to make the finger of the inner ring 112 pass from the first portion 126 to the second portion 128 of the cam and to hence disengage the inner ring 112 from the tip 22.

Figure 4D:
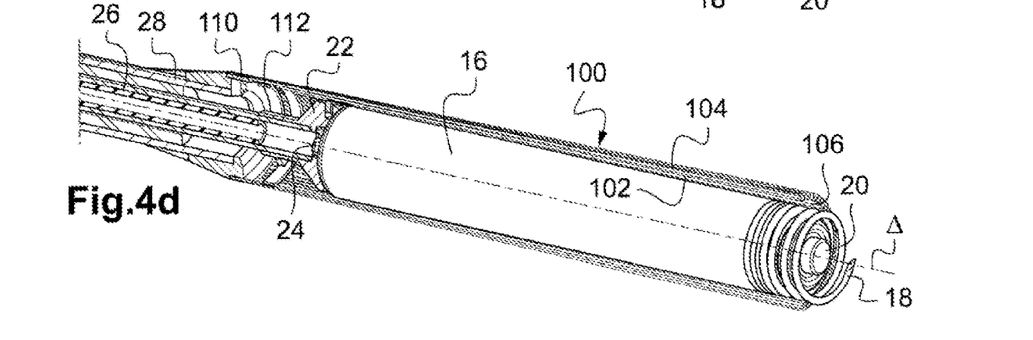

Due to the elasticity of the flexible lamellas 108, the deformable tube 110 will then recover its initial shape (corresponding to the folded position), as illustrated in FIG. 4d. On the other hand, the rear end 24 of the capsule 16 remains coupled to the tip 22, which allows the continuation of the capsule screwing (standard implantation procedure) with, in end of stroke, limitation of the screwing torque and uncoupling of the capsule from the tip 22, as described in co-pending U.S. patent application Ser. No. 16/655,198, now published as United States Patent Application Publication No. 2020/164215 A1.

Typical sizes of the deformable tube 100, for an application to the implantation of a leadless capsule, are, in the configuration illustrated in FIG. 2 (folded position):

overall diameter: 25 French (8.33 mm) for the implantation of a capsule of diameter 21 French (7 mm),
    length: 30 to 50 mm,
    the sleeve being formed of 64 titanium thin lamellas 108, on which is bonded the flexible printed circuit 116.

It will be noted that, in the above-described example, the expansion configuration is that of an inner sleeve 102 that remains cylindrical, whereas the outer sleeve 105, initially cylindrical, takes a progressively conical shape during the expansion.

As a variant, it is possible to contemplate the reverse configuration, i.e. a configuration in which the outer sleeve 104 keeps its initial cylindrical shape and in which that is the inner sleeve 102 that expands with a progressively conical shape, the cone being directed with its smallest diameter on the distal side. This variant is conceivable in an application other than the implantation of a leadless capsule, for example for a surgical intervention in which the intervention instrument is introduced into the steerable catheter 12 only after execution of the steps of expansion of the array of transducers; in this case, the inner sleeve 102 does not need to play a role of housing, and it is sufficient that, in expanded position, the diameter of the central lumen is sufficient to allow the passage of the surgical instrumentOf note, the terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes", and/or "including," when used in this specification, specify the presence of stated features, integers, steps, operations, elements, and/or components, but do not preclude the presence or addition of one or more other features, integers, steps, operations, elements, components, and/or groups thereof.

As well, the corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Having thus described the invention of the present application in detail and by reference to embodiments thereof, it will be apparent that modifications and variations are possible without departing from the scope of the invention defined in the appended claims as follows:

The invention claimed is:

1. An instrument for intracorporeal exploration and intervention, comprising:
    a dual-wall deformable tube, comprising:
        an inner sleeve extending from a proximal end to a distal end, and defining an axial lumen opening on a distal side and on a proximal side;
        an outer sleeve, coaxial to the inner sleeve and extending from a proximal end to a distal end;
        the inner sleeve and the outer sleeve being deformable between a folded position and an expanded position; and
        an annular imaging module, connected at an inner periphery to the inner sleeve and at an outer periphery to the outer sleeve; and
    an array of transducers, carried by an outer support face of the annular imaging module,
    wherein the annular imaging module is hinged to the distal end of the inner sleeve and hinged to the distal end of the outer sleeve,
    wherein the inner sleeve and the outer sleeve are mobile in relative axial translation under an axial effort exerted by the inner sleeve when pushed,
    wherein the inner sleeve, the outer sleeve, and the annular imaging module contiguously have a constant overall length, whatever a deformation thereof,
    and wherein: in the folded position, both the inner sleeve and the outer sleeve have a cylindrical shape, and the annular imaging module substantially extends in a continuation of one of the inner or outer sleeve; and
    in the expanded position, one of the inner or outer sleeve has a cylindrical shape and the other of the inner or outer sleeve has a flared shape widening on the distal side, and the annular imaging module substantially extends with the outer support face that carries the transducers of the array turned in an axial direction towards a front of the deformable tube.

2. The instrument of claim 1, wherein the transducers of the array are ultrasound transducers and are mounted on the annular imaging module with an axis of their radiation diagram directed perpendicular to the support face.

3. The instrument of claim 1, wherein in the folded position, the respective proximal ends of the inner sleeve and of the outer sleeve are moved closer to each other, and the annular imaging module substantially extends in the continuation of the inner sleeve, at least a part of the support face of the annular imaging module that carries the transducers of the array being directed radially towards an inside of the deformable tube; and
    in the expanded position, the respective proximal ends of the inner sleeve and of the outer sleeve are spaced apart from each other, the support face of the annular imaging module that carries the transducers of the array extending at least partly in a radial plane in which the transducers are directed in said axial direction parallel to a central axis of the deformable tube.

4. The instrument of claim 3, wherein, in the expanded position, the support face of the annular imaging module that carries the transducers of the array extends with a part of the transducers directed in the axial direction parallel to the central axis of the deformable tube, and another part of the transducers directed in an inclined direction crossing the central axis of the deformable tube.

5. The instrument of claim 1, wherein the annular imaging module comprises a flexible printed circuit carrying and interconnecting the transducers of the array.

6. The instrument of claim 5, wherein the flexible printed circuit is extended on the proximal side by at least one ribbon extending up to a proximal end of the deformable tube and beyond, the at least one ribbon carrying conductive tracks for a connection to the transducers of the array.

7. The instrument of claim 1,
    wherein the deformable tube comprises a set of parallel flexible lamellas each extending in an axial plane,
    wherein each of the lamellas of the set of parallel flexible lamellas is formed of a single part made of an elastic material, and
    wherein each of the lamellas of the set of parallel flexible lamellas extends from the proximal end of the inner sleeve up to the proximal end of the outer sleeve by being folded over itself at the annular imaging module.

8. The instrument of claim 7, wherein the elastic material of the lamellas of the set of parallel flexible lamellas is a metal or a metallic alloy.

9. The instrument of claim 1, wherein the inner sleeve and the outer sleeve each include a ring at their respective proximal end, a displacement of the two rings in relative axial translation enabling a transition between the folded position and the expanded position.

10. The instrument of claim 1, further comprising a steerable catheter extending the deformable tube at a proximal end of the deformable tube, the steerable catheter comprising a mobile tube housed within an intermediate tube, the mobile tube and the intermediate tube being coaxial to each other, extending from a proximal end to a distal end of the catheter and being mounted telescopically into each other with a possibility of a mutual rotation and a mutual axial translation, and wherein the inner sleeve and the outer sleeve are connected in a proximal part to, respectively, the mobile tube and the intermediate tube of the catheter.

11. The instrument of claim 10, wherein the inner sleeve is detachably connected to the mobile tube of the catheter.

12. The instrument of claim 11, wherein the inner sleeve is connected to the mobile tube of the catheter by means of a tip including a member for coupling the mobile tube of the catheter to an implantable autonomous capsule adapted to be housed within the axial lumen of the inner sleeve.

13. The instrument of claim 12, wherein the tip is adapted to be uncoupled from the inner sleeve under an effect of a rotation of the mobile tube in the intermediate tube of the catheter, the tip remaining coupled to the inner sleeve during an axial translation of the mobile tube in the intermediate tube of the catheter.

14. The instrument of claim 10, wherein the mobile tube of the catheter is connected to a surgical instrument adapted to be housed within the axial lumen of the inner sleeve.

\* \* \* \* \*